United States Patent
Uematsu et al.

(10) Patent No.: US 9,885,604 B2
(45) Date of Patent: Feb. 6, 2018

(54) OPTICAL SENSOR AND ELECTRONIC APPARATUS

(71) Applicant: Seiko Epson Corporation, Shinjuku-ku (JP)

(72) Inventors: Akira Uematsu, Suwa (JP); Yoshiyuki Terashima, Matsumoto (JP); Yoichi Sato, Suwa-gun (JP); Atsushi Matsuo, Tachikawa (JP)

(73) Assignee: Seiko Epson Corporation, Tokyo (JP)

( * ) Notice: Subject to any disclaimer, the term of this patent is extended or adjusted under 35 U.S.C. 154(b) by 502 days.

(21) Appl. No.: 14/383,421

(22) PCT Filed: Mar. 6, 2013

(86) PCT No.: PCT/JP2013/001423
§ 371 (c)(1),
(2) Date: Sep. 5, 2014

(87) PCT Pub. No.: WO2013/132852
PCT Pub. Date: Sep. 12, 2013

(65) Prior Publication Data
US 2015/0036133 A1 Feb. 5, 2015

(30) Foreign Application Priority Data

Mar. 7, 2012 (JP) .................. 2012-049983

(51) Int. Cl.
*G01J 1/06* (2006.01)
*G01B 11/26* (2006.01)
(Continued)

(52) U.S. Cl.
CPC ............ *G01J 1/06* (2013.01); *A61B 5/02427* (2013.01); *G01B 11/26* (2013.01); *G01J 1/0204* (2013.01);
(Continued)

(58) Field of Classification Search
CPC .... G01J 3/0262; G01J 1/06; G01J 3/26; G01J 3/513; G01J 1/0437; G01J 1/0204;
(Continued)

(56) References Cited

U.S. PATENT DOCUMENTS 6,590,660 B2 * 7/2003 Jung .................. G01J 1/06
250/226
7,446,359 B2 11/2008 Lee et al.
(Continued)

FOREIGN PATENT DOCUMENTS

JP 61-205827 A 9/1986
JP 2001-050814 A 2/2001
(Continued)

OTHER PUBLICATIONS

Supplementary European Search Report, dated Oct. 21, 2015, of the corresponding European Application No. 13758563.4.; (6 pages).

*Primary Examiner* — Dominic J Bologna
(74) *Attorney, Agent, or Firm* — Kilpatrick Townsend & Stockton LLP

(57) ABSTRACT

To provide an optical sensor, an electronic apparatus, etc. that suppress reduction of spectroscopic characteristics. The optical sensor includes a light receiving element, an optical filter 140 that transmits a light having a specific wavelength of incident lights with respect to a light receiving region of the light receiving element, and an angle limiting filter 120 that limits an incident angle of the incident light transmitted through the optical filter 140.

12 Claims, 12 Drawing Sheets

(51) Int. Cl.
*G01J 3/51* (2006.01)
*G01J 3/26* (2006.01)
*A61B 5/024* (2006.01)
*G01J 1/04* (2006.01)
*G01J 1/02* (2006.01)
*G01J 1/42* (2006.01)
*G01J 3/02* (2006.01)
*G01J 3/36* (2006.01)
*A61B 5/1455* (2006.01)
*H01L 27/146* (2006.01)
*A61B 5/145* (2006.01)

(52) U.S. Cl.
CPC ............ *G01J 1/0437* (2013.01); *G01J 1/0488* (2013.01); *G01J 1/42* (2013.01); *G01J 3/0229* (2013.01); *G01J 3/0256* (2013.01); *G01J 3/0262* (2013.01); *G01J 3/0289* (2013.01); *G01J 3/26* (2013.01); *G01J 3/36* (2013.01); *G01J 3/51* (2013.01); *G01J 3/513* (2013.01); *A61B 5/1455* (2013.01); *A61B 5/14532* (2013.01); *H01L 27/14625* (2013.01)

(58) Field of Classification Search
CPC .... G01J 1/42; G01J 3/0256; G01J 3/36; G01J 3/0229; G01J 1/0488; G01J 3/51; G01J 3/0289; A61B 5/02427; G01B 11/26
See application file for complete search history.

(56) References Cited

U.S. PATENT DOCUMENTS

| | | | | |
|---|---|---|---|---|
| 2007/0139765 A1* | 6/2007 | Daniel | .................... | G02B 6/08 359/443 |
| 2007/0290284 A1* | 12/2007 | Shaffer | ............... | H01L 27/1446 257/432 |
| 2010/0264297 A1* | 10/2010 | Kurahashi | .......... | G02B 27/0018 250/208.1 |
| 2011/0090505 A1 | 4/2011 | Kuze et al. | | |
| 2011/0215432 A1 | 9/2011 | Uematsu et al. | | |
| 2011/0216315 A1* | 9/2011 | Uematsu | .................. | G01J 3/02 356/326 |
| 2011/0242526 A1* | 10/2011 | Van Bommel | ............ | G01J 1/04 356/121 |
| 2012/0236297 A1 | 9/2012 | Uematsu et al. | | |
| 2013/0120760 A1* | 5/2013 | Raguin | .................. | G01B 11/24 356/612 |

FOREIGN PATENT DOCUMENTS

| | | |
|---|---|---|
| JP | 2006-013520 A | 1/2006 |
| JP | 2011-203247 A | 10/2011 |
| JP | 2012-194054 A | 10/2012 |
| WO | 2009-148134 A | 12/2009 |

* cited by examiner

FIG. 5A
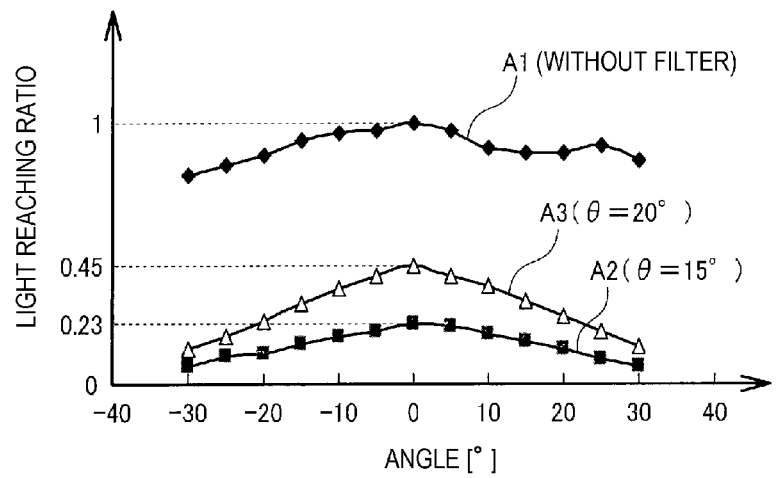
FIG. 5B
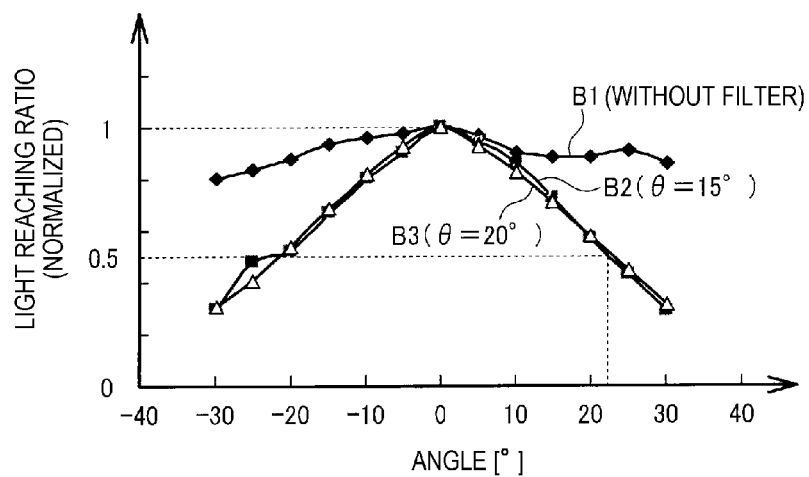
FIG. 5C
| $d^2/\lambda R$ | 0.72 | 1.32 |
|---|---|---|
| $\theta$ (d) | 15° | 20° |
| HALF-VALUE ANGLE | 22.5° ~23° | 21° ~22.5° |
| LIGHT REACHING RATIO | 22.9% | 44.8% |

FIG. 6A
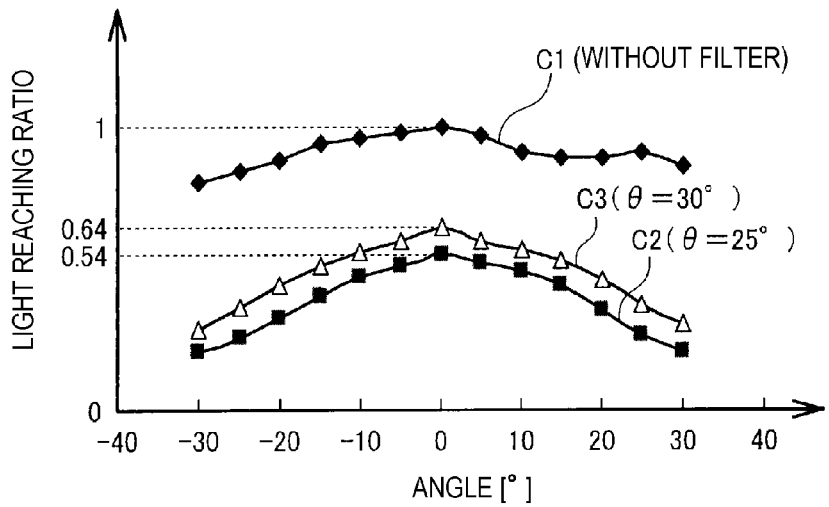
FIG. 6B
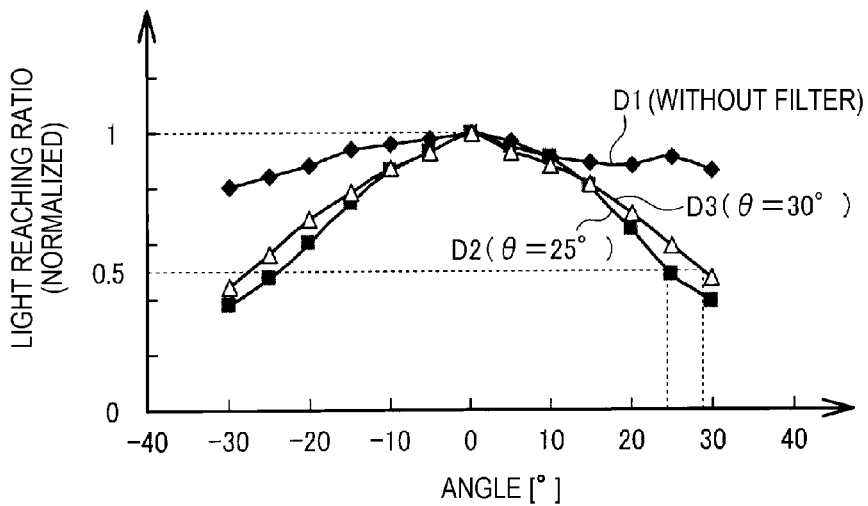
FIG. 6C
| $d^2/\lambda R$ | 2.17 | 3.34 |
|---|---|---|
| $\theta$ (d) | 25° | 30° |
| HALF-VALUE ANGLE | 24°～25° | 28°～29° |
| LIGHT REACHING RATIO | 54.4% | 64.1% |

| WAVELENGTH λ | 500nm | 900nm |
|---|---|---|
| $d=\sqrt{2\lambda R}$ ($d^2/\lambda R=2$) | 2.25 μm | 3.0 μm |
| BOUNDARY POINT | 2.3 μm | 3.0 μm |

OPTICAL SENSOR AND ELECTRONIC APPARATUS

This application is a National Phase application of International Application No. PCT/JP2013/001423, filed Mar. 6, 2013, which claims priority to Japanese Patent Application No.: 2012-049983, filed Mar. 7, 2012, the entireties of which are all hereby incorporated by reference.

TECHNICAL FIELD

This invention relates to an optical sensor, an electronic apparatus, etc.

BACKGROUND ART

For example, Patent Literature 1 has disclosed a technology of preventing crosstalk of light between a light absorbing film (light blocking material) that an image sensor as a kind of optical sensor has and an adjacent photoelectric conversion element (light receiving element).

CITATION LIST

Patent Literature

PTL 1: JP-A-2006-13520

SUMMARY OF INVENTION

Technical Problems

An optical sensor in which an angle limiting filter that limits an incident angle of an incident light to a light receiving element is formed using the light blocking material as described above, for example, and a spectroscopic filter is formed on the angle limiting filter is considered. For example, the angle limiting filter is used for improving spectroscopic characteristics of the spectroscopic filter. In the case where the spectroscopic filter is formed on the angle limiting filter, if the light incident from the side surface of the spectroscopic filter passes through the angle limiting filter, reduction of spectroscopic characteristics is problematic.

According to some aspects of the invention, an optical sensor, an electronic apparatus, etc. that suppress reduction of spectroscopic characteristics may be provided.

Solution to Problems

An aspect of the invention relates to an optical sensor including a light receiving element, an optical filter that transmits a light having a specific wavelength of incident lights with respect to a light receiving region of the light receiving element, and an angle limiting filter that limits an incident angle of the incident light transmitted through the optical filter, wherein, supposing that a limitation angle of the angle limiting filter is $\theta A$, a height from an upper surface of the angle limiting filter to an upper surface of the optical filter is RTP, and a distance from an end of the optical filter to an end of an aperture of the angle limiting filter in a plan view with respect to the upper surface of the angle limiting filter is an overlap distance OV, $\tan^{-1}(OV/RTP) > \theta A$ is satisfied.

According to the aspect of the invention, the overlap distance OV as the distance from the end of the optical filter to the end of the aperture of the angle limiting filter satisfies $\tan^{-1}(OV/RTP) > \theta A$. Thereby, reduction of spectroscopic characteristics may be suppressed.

Further, in the aspect of the invention, supposing that a width of the aperture of the angle limiting filter is d and a height of the angle limiting filter is RA, the limitation angle may be $\theta A = \tan^{-1}(d/RA)$.

Accordingly, the limitation angle may be set by adjustment of the aperture width and the height of the angle limiting filter, and the overlap distance that satisfies $\tan^{-1}(OV/RTP) > \theta A$ with respect to the set limitation angle may be set.

Furthermore, the aspect of the invention may further include a protective film formed between the angle limiting filter and the optical filter, wherein, supposing that a height of the protective film is RP and a height of the optical filter is RT, the height from the upper surface of the angle limiting filter to the upper surface of the optical filter may be RTP=RP+RT.

Note that, in the aspect of the invention, not limited to that, but, in the case where the protective film is not provided, RTP=RT may hold. Alternatively, in the case where another layer having a thickness RP' is further provided between the angle limiting filter and the optical filter, RTP=RP+RP'+RT may hold.

Further, in the aspect of the invention, supposing that a wavelength of the incident light is $\lambda$, the height of the angle limiting filter is RA, and the width of the aperture of the angle limiting filter is d, $d^2/(\lambda \times RA) \geq 2$ may be satisfied.

Accordingly, the angle limiting filter may be formed in a size that satisfies the condition of $d^2/(\lambda \times RA) \geq 2$. Thereby, the limitation angle for limiting the incident angle of the light reaching the light receiving element may be controlled with high accuracy.

Furthermore, in the aspect of the invention, the limitation angle may satisfy $\theta A = \tan^{-1}(d/RA) < 60°$.

Since the limitation angle of 60° is obtained without the angle limiting filter, the angle limitation of the angle limiting filter may be enabled by setting the limitation angle that satisfies $\tan^{-1}(d/RA) < 60°$.

Further, in the aspect of the invention, the optical sensor may be a spectroscopic sensor for spectroscopically separating the incident light.

Furthermore, in the aspect of the invention, the optical sensor may be an illuminance sensor for measuring illuminance of the incident light.

In addition, in the aspect of the invention, the optical sensor may be an elevation sensor for measuring an elevation angle of a light source.

Further, another aspect of the invention relates to an electronic apparatus including any one of the optical sensors.

BRIEF DESCRIPTION OF DRAWINGS

FIGS. 5(A) to 5(C) show comparative examples of angular characteristics of light reaching ratios.

FIGS. 6(A) to 6(C) show angle characteristic examples of light reaching ratios in the embodiment.

DESCRIPTION OF EMBODIMENTS

As below, preferred embodiments of the invention will be explained in detail. Note that the embodiments explained as below do not unduly limit the invention described in claims, and all of the configurations explained embodiments are not necessarily essential as solving means of the invention.

1. Comparative Example

Figure 1:
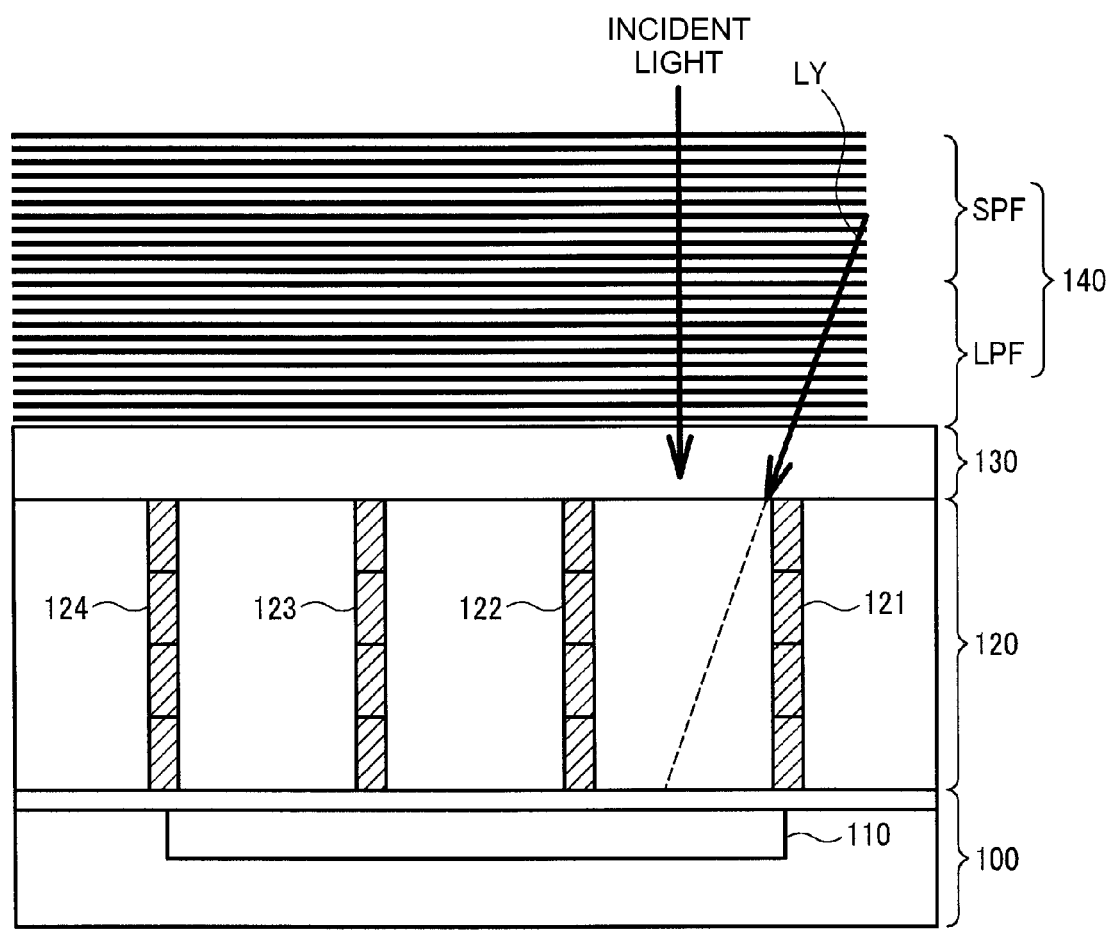
FIG. 1 shows a comparative example of an optical sensor.

FIG. 1 shows a comparative example of an optical sensor of the embodiment. The optical sensor in FIG. 1 includes a semiconductor substrate 100 on which an impurity region 110 for light receiving element (photosensor) is formed, an angle limiting filter 120 with light blocking materials 121 to 124 formed thereon by a wiring process on the semiconductor substrate 100, a protective film 130 formed on the angle limiting filter 120, and a bandpass filter 140 formed on the protective film 130.

The bandpass filter 140 is a thin-film filter in which thin films are stacked, for example. The thin-film filter has different transmission wavelengths in response to incident angles, and, if the incident angle is not limited, the wavelength band detected by a light receiving element formed by the impurity region 110 and the semiconductor 100 becomes broader. In the comparative example in FIG. 1, the incident angle of the light incident to the light receiving element is limited by the angle limiting filter 120, and thereby, the wavelength band detected by the light receiving element may be narrowed.

Now, the designed characteristics of the thin-film filter forming the bandpass filter 140 are not exerted until the incident light passes through all of the stacked layers. That is, like light LY shown in FIG. 1, the light entering from the wall surface of the bandpass filter 140 and passing through only part of the stacked layers does not have band limitation characteristics as designed. When the light passes through the angle limiting filter 120 and is detected by the light receiving element, reduction of the band limitation characteristics of the optical sensor is problematic.

Figure 2A:
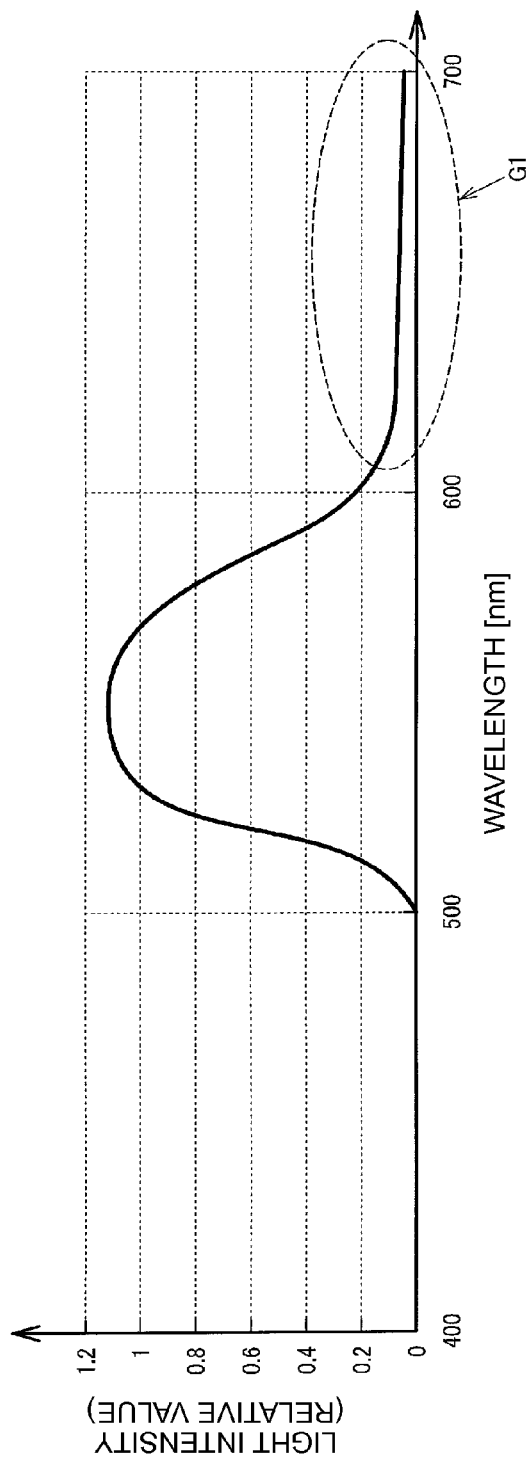
FIG. 2(A) shows a spectroscopic characteristic example of the comparative example of the optical sensor.
Figure 2B:
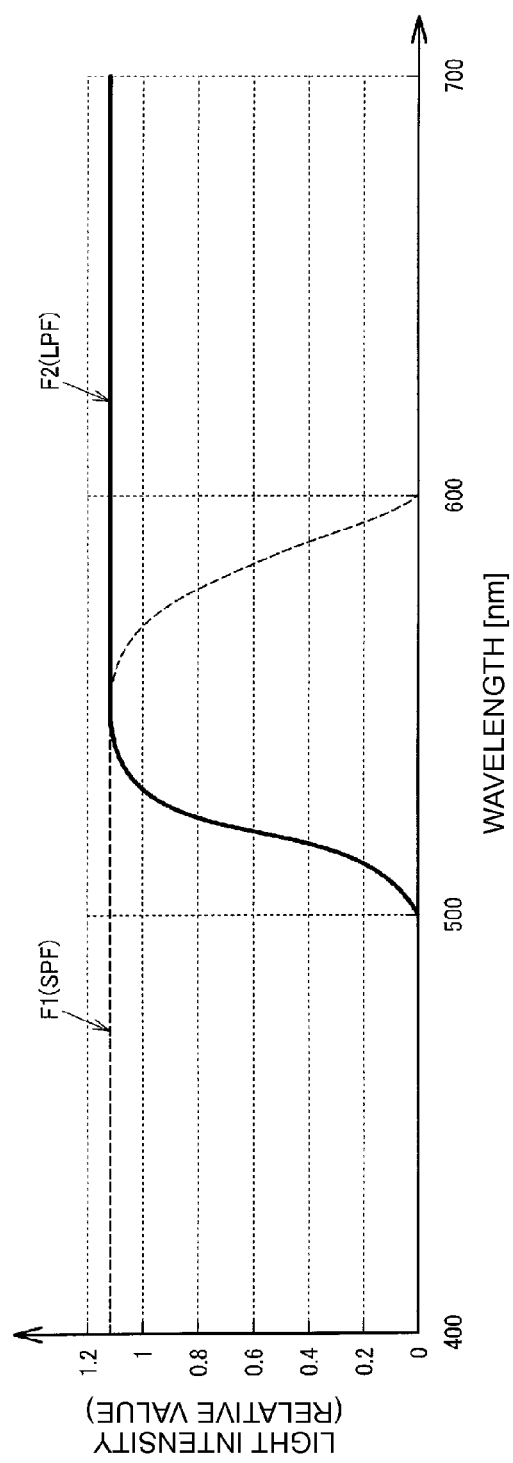
FIG. 2(B) shows a spectroscopic characteristic example of a short-pass filter and a long-pass filter.

For example, FIG. 2(A) shows a spectroscopic characteristic example when the light beam LY reaches the light receiving element. As shown in FIG. 1, it is assumed that the bandpass filter 140 includes a short-pass filter SPF and a long-pass filter LPF, for example. As shown by F1 in FIG. 2(B), the short-pass filter SPF is a thin-film filter that transmits the band at the shorter wavelength side than a predetermined wavelength λS, and, as shown by F2, the long-pass filter LPF is a thin-film filter that transmits the band at the longer wavelength side than a predetermined wavelength λL. Through these filters SPF, LPF, the band of the incident light is limited within the wavelength range from λL to λS.

In this case, assuming that the light beam LY entering from the wall surface of the bandpass filter 140 passes through only a part of the short-pass filter SPF, the band limitation characteristics of the short-pass filter SPF are reduced and the lights at the longer wavelength side also pass. As shown by G1 in FIG. 2A, in the bandpass filter 140 as a whole, the lights at the longer wavelength side reach the light receiving element, and the rejection band at the longer wavelength side rises and the rejection rate becomes lower.

2. Optical Sensor

Figure 3:
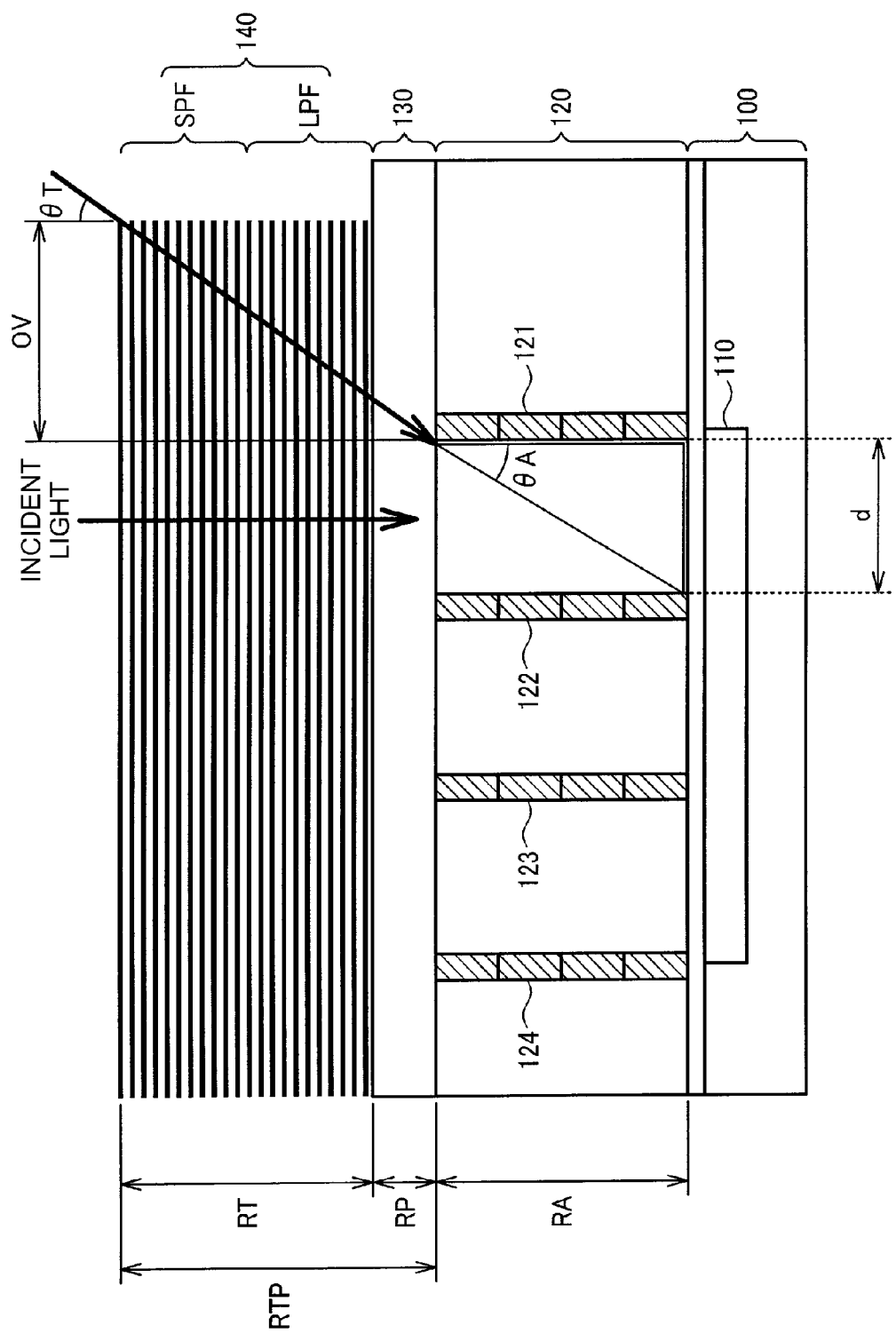
FIG. 3 shows a configuration example of an optical sensor of an embodiment.

FIG. 3 shows a configuration example of an optical sensor that solve the problem that the rejection rate of the bandpass filter becomes lower.

The optical sensor in FIG. 3 includes a semiconductor substrate 100 on which an impurity region 110 for light receiving element is formed, an angle limiting filter 120 with light blocking materials 121 to 124 formed thereon by a wiring process on the semiconductor substrate 100, a protective film 130 formed on the angle limiting filter 120, and a bandpass filter 140 (in the broad sense, an optical filter) formed on the protective film 130. Here, "on" of "on the semiconductor substrate 100" or the like refers to a direction toward a side on which the angle limiting filter 120 etc. are formed of the directions perpendicular to the surface of the semiconductor substrate 100.

The bandpass filter 140 includes a long-pass filter LPF formed on the protective film 130 and a short-pass filter SPF formed on the long-pass filter LPF. The long-pass filter LPF and the short-pass filter SPF are thin-film filters in which thin films are stacked and have the spectroscopic characteristics explained in FIG. 2(B), for example. Note that the long-pass filter LPF and the short-pass filter SPF may be vertically replaced.

The impurity region 110 is an impurity region of first conductivity-type (e.g., n-type) and the semiconductor substrate 100 is an impurity region of second conductivity-type (e.g., p-type). A light receiving element is formed by p-n junction of the impurity region 110 and the semiconductor substrate 100. The light receiving element is a photodiode, for example.

The angle limiting filter 120 is formed by a wiring process of a semiconductor process. When a light linearly entering the light receiving element from the top surface of the angle limiting filter 120 is assumed, if the incident angle is smaller than θA, the incident light linearly reaches the light receiving element. If the incident angle is larger than θA, the incident light is blocked by the light blocking materials 121 to 124 and does not directly reach the light receiving element. The angle θA is referred to as "limitation angle (control angle)". Note that, if the incident light is larger than θA, the light due to diffraction or reflection may indirectly reach the light receiving element. By the blocking of lights, the incident light at the incident angle larger than the limitation angle θA may be prevented from directly reaching the light receiving element. The light blocking materials 121 to 124 are materials that block at least the lights in the transmission band of the bandpass filter 140. Specifically, the light blocking materials 121 to 124 are metal layers (e.g., aluminum wiring layers) used for metal wiring. The protective film 130 stacked on the angle limiting filter 120 is formed using a material that transmits at least the lights in the transmission band of the bandpass filter 140. Specifically, the protective film 130 is formed by an insulating layer (e.g., an $SiO_2$ layer) of the semiconductor process.

Note that the more detailed configuration and formation process of the optical sensor of the embodiment will be described later with FIGS. 5(A) to 11.

As shown in FIG. 3, suppose that the height of the bandpass filter 140 is RT, the height of the protective film is RP, and the height of the angle limiting filter 120 is RA. For example, RT=5 μm, RP=1 μm, and RA=5 μm. Here, "height" is a height (or thickness) in the direction perpendicular to the surface of the semiconductor substrate 100, and, for example, regarding the bandpass filter 140, corresponds to a distance from the lower surface to the upper surface of the bandpass filter 140.

Further, suppose that the width of the aperture of the angle limiting filter 120 is d. For example, d=3 μm. Here, "aperture" of the angle limiting filter 120 is a region where no blocking material exists on the surface at the side on which the incident light enters, and where the incident light enters in a plan view with respect to the angle limiting filter 120. Note that the outer circumference of the aperture is not necessarily closed by the light blocking material, but the light blocking material may be discontinuously provided along the outer circumference of the aperture. Further, "aperture width" refers to a distance from the wall surface of the light blocking material to the wall surface of the light blocking material opposed to that wall surface, and, when the aperture has a rectangular shape, for example, corresponds to the length of the side of the rectangle. "The wall surface of the light blocking material" is a boundary surface between the material filling the aperture (e.g., $SiO_2$) and the light blocking material, and the surface intersecting with (in the narrow sense, perpendicular to) the surface of the semiconductor substrate 100.

From the height RA of the angle limiting filter 120 and the aperture width d, the limitation angle is $\theta A=\tan^{-1}(d/RA)$. For example, when RA=5 μm and d=3 μm, $\theta A=31°$. The lights at the incident angles larger than the limitation angle $\theta A$ are blocked and do not enter the light receiving element. With respect to the limitation angle $\theta A$, the overlap distance OV between the angle limiting filter 120 and the bandpass filter 140 is set to satisfy the following formula (1). Here, "angles" including "limitation angle" refer to angles with respect to the direction perpendicular to the surface of the semiconductor substrate 100.

$$\theta A=\tan^{-1}(d/RA)<\theta T=\tan^{-1}(OV/(RT+RP)) \quad (1)$$

As shown in FIG. 3, of the incident lights reaching the outermost aperture end of the angle limiting filter 120, the lights at the incident angles larger than the angle $\theta T=\tan^{-1}(OV/(RT+RP))$ are lights that have passed through the wall surface of the bandpass filter 140. That is, the limitation angle $\theta A$ is set to an angle smaller than the angle $\theta T$ as in the above formula (1), the lights that have passed through the wall surface of the bandpass filter 140 may be blocked. Here, "overlap distance" refers to a distance from a boundary between the formation region and the non-formation region of the bandpass filter 140 (the wall surface of the bandpass filter 140) to the outermost aperture end of the angle limiting filter 120 in the plan view with respect to the semiconductor substrate 100. Further, "outermost aperture end" corresponds to the inner wall surface of the aperture formed at the outermost side of the angle limiting filter 120 in the plan view with respect to the semiconductor substrate 100.

Figure 4:
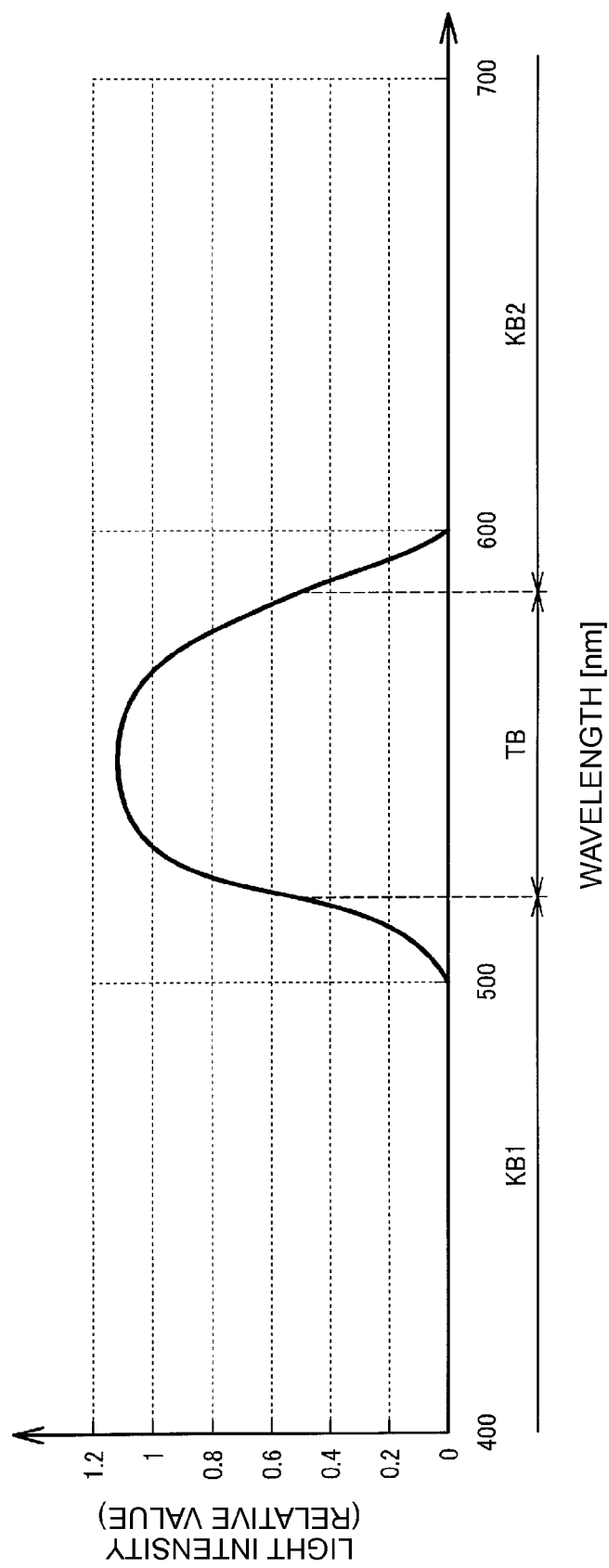
FIG. 4 shows a spectroscopic characteristic example of the optical sensor of the embodiment.

FIG. 4 shows a spectroscopic characteristic example of the optical sensor of the embodiment. In the optical sensor of the embodiment, the lights that have passed through the wall surface of the bandpass filter 140 do not enter the light receiving element, and thus, the original character of the bandpass filter 140 may be exhibited. That is, as shown in FIG. 4, the light intensity in the rejection bands KB1, KB2 is sufficiently smaller than that in the transmission band TB, and the band limitation characteristics do not become lower than those of the above described comparative example.

Note that, in the above description, the case where the optical filter is the bandpass filter and the bandpass filter 140 includes the short-pass filter SPF and the long-pass filter LPF has been explained as an example, however, the embodiment is not limited to the case. For example, the optical filter may be another filter having spectroscopic characteristics than the bandpass filter. Further, the bandpass filter 140 may not include the separately stacked short-pass filter SPF and long-pass filter LPF.

According to the above described embodiment, as shown in FIG. 3, the optical sensor includes the light receiving element, the optical filter 140 that transmits a light having a specified wavelength of incident lights to the light receiving region of the light receiving element, and the angle limiting filter 120 that limits the incident angle of the incident light transmitted through the optical filter 140. Supposing that the limitation angle of the angle limiting filter 120 is $\theta A$ and the height from the upper surface (aperture surface, incident surface) of the angle limiting filter 120 to the upper surface (incident surface) of the optical filter is RTP, the overlap distance OV as the distance from the end of the optical filter 140 to the end of the aperture of the angle limiting filter in the plan view with respect to the upper surface of the angle limiting filter 120 satisfies $\tan^{-1}(OV/RTP)>\theta A$.

Here, "upper surface of angle limiting filter 120" refers to the upside surface of the layer of the angle limiting filter 120 formed by the semiconductor process and a boundary surface between the layer of the angle limiting filter 120 and the layer formed on the angle limiting filter 120 (e.g., the protective film 130). Further, "upper surface of optical filter 140" refers to the upside surface of the stacked optical filter 140. "Upper" is a direction away from the surface of the semiconductor substrate 100, and the normal direction at the side at which the angle limiting filter 120 etc. are formed of the normal directions of the surface of the semiconductor substrate 100. Furthermore, "light receiving region" refers to a region where the incident lights that have passed through the angle limiting filter 120 may reach in the impurity region 110 forming the light receiving element.

Accordingly, as has been explained with FIG. 3 etc., the lights passing through the angle limiting filter 120 are lights that have entered from the upper surface of the optical filter 140 and have passed through all layers of the optical filter 140. Thereby, as has been explained with FIG. 4 etc., the reduction of the rejection rates of the rejection bands KB1, KB2 by the lights that have passed through only part of the layers of the optical filter 140 may be prevented.

Further, in the embodiment, supposing that the aperture width of the angle limiting filter 120 is d and the height of the angle limiting filter 120 is RA, the limitation angle is $\theta A=\tan^{-1}(d/RA)$.

Accordingly, the limitation angle $\theta A$ may be set by adjustment of the aperture width d and the height RA of the angle limiting filter 120, and the overlap distance OV that satisfies $\tan^{-1}(OV/RTP)>\theta A$ with respect to the limitation angle $\theta A$ may be set.

Further, in the embodiment, when the protective film 130 formed between the angle limiting filter 120 and the optical filter 140 is included and the height (thickness) of the protective film 130 is RP and the height (thickness) of the optical filter 140 is RT, the height from the upper surface of the angle limiting filter 120 to the upper surface of the optical filter 140 is RTP=RP+RT.

Note that, in FIG. 3, the case of RTP=RP+RT has been explained as an example, however, the embodiment is not limited to that. For example, the protective film 130 may be omitted and RTP=RT may hold. Alternatively, another layer having a thickness of RP' may be further provided between the angle limiting filter 120 and the optical filter 140 and RTP=RP+RP'+RT may hold.

3. Aperture Width and Height of Angle Limiting Filter

Next, a method of setting the aperture width d and the height RA of the angle limiting filter 120 will be explained. In the embodiment, an overlap distance OV that satisfies the above formula (1) is set with respect to the aperture width d and the height RA set according to the method to be described. Note that, as below, the height RA of the angle limiting filter 120 will be referred to as "R" and the limitation angle θA will be referred to as "θ".

In the embodiment, the aperture width d and the height R of the angle limiting filter are set to satisfy the following formula (2). Thereby, angle controllability that the measured limitation angle is controllable by adjustment of the aperture width d and the height R and a light reaching ratio as a ratio of an amount of light entering the aperture of the angle limiting filter and an amount of light reaching the light receiving element may be improved. In this regard, the detailed explanation will be made using FIGS. 5(A) to 7(B).

$$d^2/(\lambda \times R) \geq 2 \tag{2}$$

First, FIGS. 5(A) to 5(C) show light reaching ratio characteristics when $d^2/(\lambda \times R) < 2$ as comparative examples. FIGS. 5(A) to 5(C) show measured values of light reaching ratios when the incident angle of the incident light is changed for the wavelength λ=0.5 μm and the height R=5 μm.

FIG. 5(A) shows light reaching ratio characteristics supposing the light reaching ratio of the incident angle of 0° without the angle limiting filter is "1". As shown by A1 in FIG. 5(A), the light reaching ratio gradually attenuates as the incident angle (the absolute value of the incident angle) increases without the angle limiting filter. As shown by A2, when the limitation angle θ=15° and the aperture width d=1.34 μm, the maximum value of the light reaching ratio is 0.23. As shown by A3, when the limitation angle θ=20° and the aperture width d=1.82 μm, the maximum value of the light reaching ratio is 0.45.

As described above, in the angle limiting filter of the comparative example, the light reaching ratio is lower than 50%, and, if the incident light is dark, the sensor sensitivity may be insufficient.

FIG. 5(B) shows the light reaching ratio characteristics of FIG. 5(A) normalized to "1" at the incident angle of 0°. Note that, as below, the explanation will be made with the incident angle when the light reaching ratio becomes ½ of the light reaching ratio at the incident angle of 0° as the limitation angle θ, however, the embodiment is not limited to that, but θ may be defined by the incident angle when the light reaching ratio is another ratio.

B1 in FIG. 5(B) shows a measured value without the angle limiting filter, B2 shows a measured value when a designed limitation angle is θ=15°, and B3 shows a measured value when the designed limitation angle is θ=20°. Here, "designed limitation angle" refers to θ=tan⁻¹(d/R). As shown by B2, B3, both of the actually measured limitation angles are about 22° and the designed limitation angles are not obtained, and it is known that the angle controllability is poor.

FIG. 5(C) shows the above described measured values. As shown in FIG. 5(C), in both cases of θ=15° and 20°, $d^2/(\lambda \times R) < 2$, and it is known that sufficient angle controllability and light reaching ratio may not be obtained in this range.

Next, FIGS. 6(A) to 6(C) show light reaching ratio characteristics when $d^2/(\lambda \times R) \geq 2$ of the above described formula (2) is satisfied. FIGS. 6(A) to 6(C) show measured values of light reaching ratios when the incident angle of the incident light is changed for the wavelength λ=0.5 μm and the height R=5 μm.

FIG. 6(A) shows light reaching ratio characteristics supposing the light reaching ratio of the incident angle of 0° without the angle limiting filter is "1". As shown by C1 in FIG. 6(A), the characteristics without the angle limiting filter are not different from those of the comparative example. As shown by C2, when the limitation angle θ=25° and the aperture width d=2.33 μm, the maximum value of the light reaching ratio is 0.54. As shown by C3, when the limitation angle θ=30° and the aperture width d=2.89 μm, the maximum value of the light reaching ratio is 0.64. As described above, $d^2/(\lambda \times R) \geq 2$ of the above described formula (2) is satisfied, and thereby, the maximum value of the light reaching ratio (the light reaching ratio at the incident angle of 0°) is higher than 50%, and, even when the incident light is dark, the sufficient sensor sensitivity may be obtained.

FIG. 6(B) shows the light reaching ratio characteristics of FIG. 6(A) normalized to "1" at the incident angle of 0°. D1 in FIG. 6(B) shows a measured value without the angle limiting filter, D2 shows a measured value when a designed limitation angle is θ=25°, and D3 shows a measured value when the designed limitation angle is θ=30°. Here, "designed limitation angle" refers to θ=tan⁻¹(d/R). As shown by D2, D3, the actually measured limitation angles (the limitation angles when the light reaching ratio is 0.5) are 24° to 25° and 28° to 29°, respectively. These limitation angles are nearly the same as the designed limitation angles, and it is known that the desired angle controllability is obtained.

FIG. 6(C) shows the above described measured values. As shown in FIG. 6(C), in both cases of θ=25° and 30°, the condition of $d^2/(\lambda \times R) \geq 2$ is satisfied, and it is known that the angle controllability and the light reaching ratio may be sufficiently obtained in this range. As described above, the angle controllability is improved, and thereby, desired wavelength resolution may be realized when the optical sensor is a spectroscopic sensor, for example. Further, the light reaching ratio is larger than that in the comparative example, sensing can be performed with high sensibility with the less amount of light.

For example, if the angle limiting filter with θ=15° of the above described comparative example is designed in the range of $d^2/(\lambda \times R) \geq 2$, d=4.02 μm, R=15 μm may be set as expressed by the following formula (3). Further, regarding the angle limiting filter with θ=20°, d=3.64 μm, R=10 μm may be set as expressed by the following formula (4).

$$d^2/(\lambda \times R) = 4.02^2/(0.5 \times 15) = 2.15 \geq 2 \tag{3}$$

$$d^2/(\lambda \times R) = 3.64^2/(0.5 \times 10) = 2.65 \geq 2 \tag{4}$$

Figures 7A, 7B:
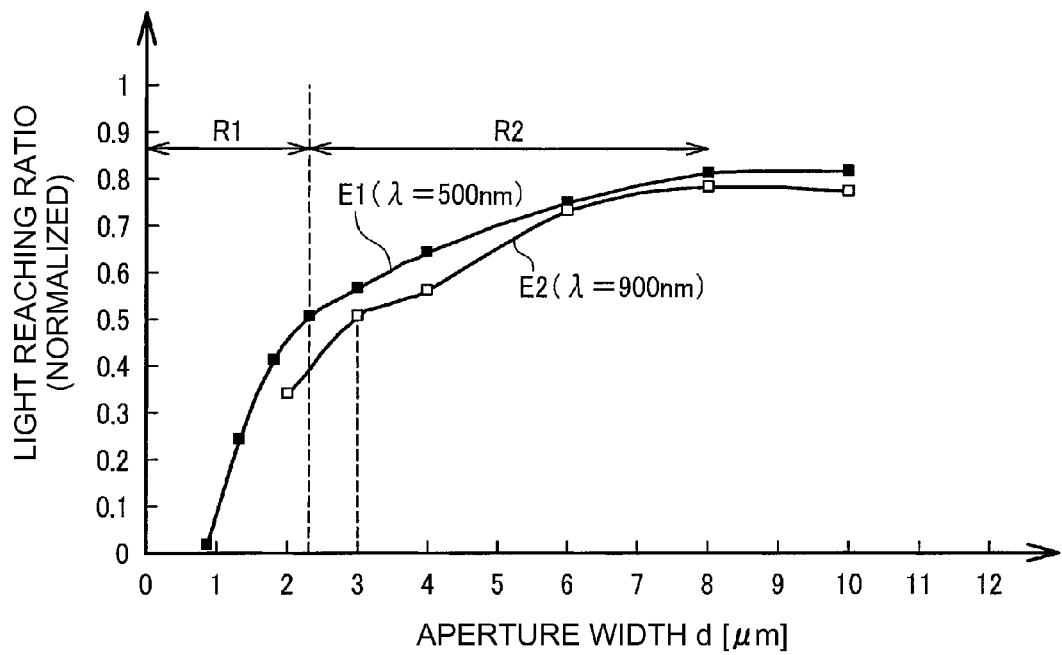
FIGS. 7(A) and 7(B) show aperture width characteristic examples of light reaching ratios in the embodiment.

Next, a relationship between the condition of the above described formula (2) and the maximum light reaching ratio will be described in more detail. FIG. 7(A) shows light reaching ratio characteristics of the incident light at the incident angle of 0°. E1 in FIG. 7(A) shows measured values for the wavelength λ=0.5 µm and the height R=5 µm when the aperture width d is changed. E2 shows measured values for the wavelength λ=0.9 µm and the height R=5 µm when the aperture width d is changed.

In the characteristics shown by E1, the gradient of the tangent rapidly changes near the aperture width d=2.3 µm. Hereinafter, the point is referred to as "boundary point". It is known that, when the aperture width d is smaller than the boundary point, the light reaching ratio rapidly falls. That is, supposing that a range of d≤2.3 µm to the boundary point is a first characteristic region R1, the light reaching ratio rises with a constant (nearly constant) first gradient in the first characteristic region R1. Supposing that a range of 2.3 µm≤d≤8 µm equal to or larger than the boundary point is a second characteristic region R2, the light reaching ratio changes with a constant (nearly constant) second gradient smaller than the first gradient in the second characteristic region R2.

In the characteristics shown by E2, the boundary point is d=3 µm, and the first characteristic region is d≤3 µm and the second characteristic region is 3 µm≤d≤8 µm. Also, in the characteristics shown by E2, it is known that, when the aperture width d is smaller than the boundary point, the light reaching ratio is lower to below 0.5.

As shown in FIG. 7(B), the above described boundary point is equal (nearly equal) to the value of d when $d^2/(\lambda \times R)=2$. That is, it is known that the angle limiting filter is formed so that the aperture width d may be larger than the boundary point, and thereby, the condition of $d^2/(\lambda \times R) \geq 2$ is satisfied, and the angle controllability and the light reaching ratio may be improved. As described above, in the embodiment, the size of the angle limiting filter may be determined from also the light reaching ratio characteristics with respect to the aperture width d.

Note that, in the embodiment, it is desirable to form the angle limiting filter to be near $d^2/(\lambda \times R)=2$ as the boundary point. At the boundary point, the height R of the angle limiting filter may be minimized and the optical sensor may be downsized. That is, since the limitation angle $\theta=\tan^{-1}(d/R)$, the aspect ratio d/R is fixed when θ is determined. Therefore, at the boundary point at which d is minimum in the range in which $d^2/(\lambda \times R) \geq 2$ is satisfied, R is also minimized.

According to the above described embodiment, as has been explained with the above described formula (2), when the wavelength of the incident light is λ, the height of the angle limiting filter is R (=RA), and the width of the aperture of the angle limiting filter is d, $d^2/(\lambda \times R) \geq 2$ is satisfied.

Thereby, the incident limitation angle θ of the incident light may be controlled with high accuracy. Further, the light reaching ratio may be improved. That is, compared to the measured values for $d^2/\lambda R<2$ shown in FIG. 5(C), the desired limitation angle may be realized and the light reaching ratio may be raised in the measured values for $d^2/\lambda R \geq 2$ shown in FIG. 6(C).

Further, in the embodiment, the limitation angle θ(=θA) of the angle limiting filter satisfies $\theta=\tan^{-1}(d/R)<60°$.

Now, without the angle limiting filter, suppose that an incident light with intensity Li enters the light receiving element at an incident angle α. In this case, light intensity Lp on the light receiving surface of the light receiving element is expressed by Lp=Li×cos α.

Regarding Lp=Li×cos α, Lp/Li=½ at α=60°, and is equal to that the control angle is 60°. That is, when the incident angle at which the light reaching ratio is ½ is defined as the limitation angle θ, the limitation angle is θ=60° without the angle limiting filter. Accordingly, if there is an angle limiting filter with the control angle θ>60°, the limitation angle is θ=60° and the angle controllability of the angle limiting filter is lost. In this regard, according to the embodiment, the limitation angle is set to θ<60°, and thereby, the angle controllability of the angle limiting filter may be exerted.

4. Optical Sensor

The detailed configuration example of the optical sensor of the above described embodiment will be explained. Note that, as below, the case where the optical sensor is a spectroscopic sensor that performs spectrometric measurement with respect to an object to be measured in a plurality of wavelength bands will be explained as an example, however, the embodiment is not limited to that as will be described later.

Figure 8:
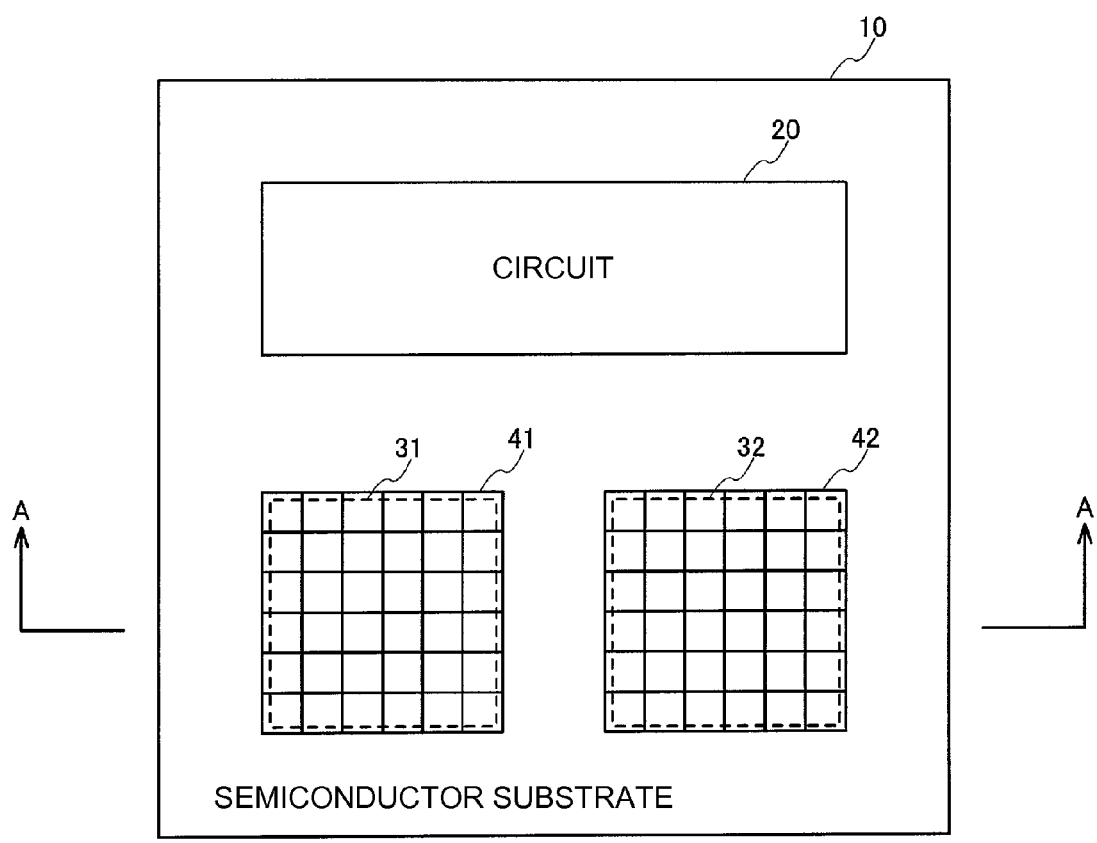
FIG. 8 is a planar view of a configuration example of a spectroscopic sensor.

FIG. 8 is a planar view with respect to a semiconductor substrate 10 on which the spectroscopic sensor is formed. FIG. 8 is the planar view as seen from the surface side on which a circuit 20, an angle limiting filter 41, etc. are formed in a plan view as seen from a direction perpendicular to the surface of the semiconductor substrate 10. As will be described later, multilayer filters are formed on the angle limiting filters 41, 42, however, the illustration thereof will be omitted for simplicity in FIG. 8.

The spectroscopic sensor shown in FIG. 8 includes the semiconductor substrate 10, the circuit 20, a first photodiode 31 (in the broad sense, a first light receiving element, an impurity region for first light receiving element), a second photodiode 32 (in the broad sense, a second light receiving element, an impurity region for second light receiving element), the first angle limiting filter 41, and the second angle limiting filter 42.

The semiconductor substrate 10 includes a P-type or N-type silicon substrate (silicon wafer), for example. On the semiconductor substrate 10, the circuit 20, the photodiodes 31, 32, the angle limiting filters 41, 42 are formed by the semiconductor process.

The angle limiting filters 41, 42 are formed in lattice shapes in the plan view, for example, and limit incident angles of incident lights to the photodiodes 31, 32. The circuit 20 includes an amplifier, an A/D conversion circuit, etc. that process output signals from the photodiodes 31, 32, for example.

Note that the spectroscopic sensor of the embodiment is not limited to the configuration in FIG. 8, but various modifications by omitting part (circuit 20) of the component elements thereof or adding another component element may be made. For example, the numbers of the photodiodes and the angle limiting filters may be two as described above, or one or more. Further, the angle limiting filters 41, 42 may have the lattice shapes in the plan view as described above, or other shapes.

Figure 9:
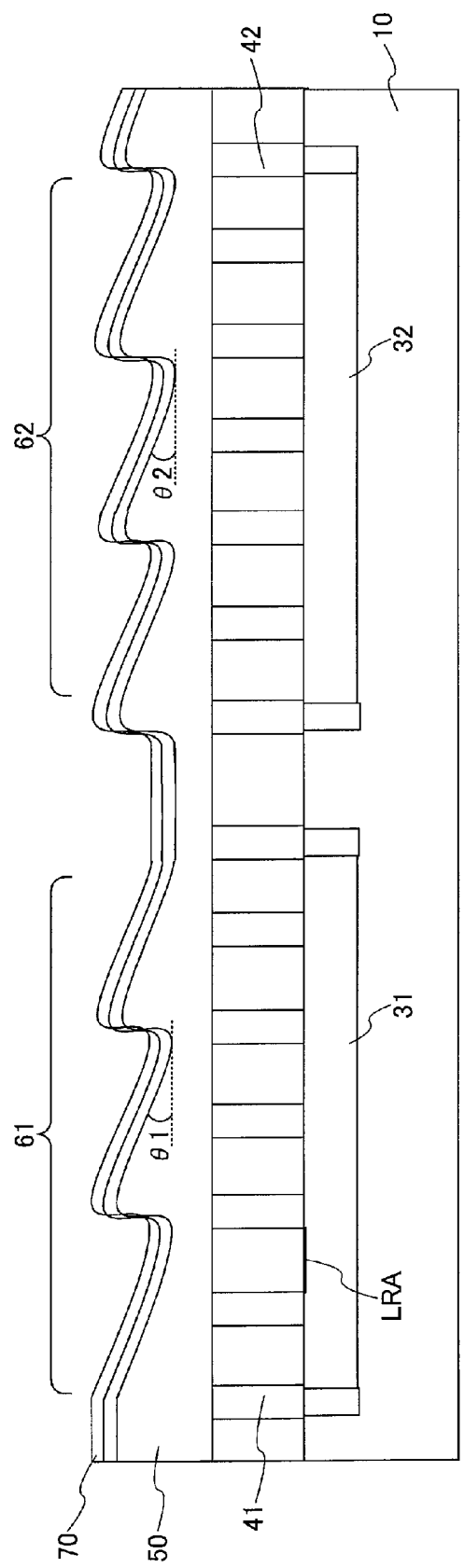
FIG. 9 is a sectional view of the configuration example of the spectroscopic sensor.

FIG. 9 shows a sectional view of the spectroscopic sensor. FIG. 9 is the sectional view along AA-section shown in FIG. 8. The spectroscopic sensor shown in FIG. 9 includes the semiconductor substrate 10, the photodiodes 31, 32, the angle limiting filters 41, 42, an inclined structure 50 (angular structure), a first optical bandpass filter 61 (first multilayer filter, first dielectric filter), and a second optical bandpass filter 62 (second multilayer filter, second dielectric filter).

The photodiodes 31, 32 are formed on the semiconductor substrate 10. As will be described later, the photodiodes 31, 32 are formed by formation of impurity regions by ion implantation or the like. For example, the photodiodes 31, 32 are realized by P-N junction between N-type impurity regions formed on P-substrates and P-substrates. Alternatively, the photodiodes are realized by P-N junction between P-type impurity regions formed on deep N-wells (N-type impurity regions) and the deep N-wells.

The angle limiting filters 41, 42 are formed using a light blocking material (e.g., light absorbing material or light reflection material) having light blocking effects with respect to the wavelengths detected by the photodiodes 31, 32. Specifically, the angle limiting filters 41, 42 are formed at the wiring forming step of the semiconductor process and formed using conducting plugs such as tungsten (in the broad sense, light absorbing material) plugs, for example. Further, the angle limiting filters 41, 42 may be formed to include conducting layers such as aluminum (in the broad sense, light reflection material) wiring layers.

The aspect ratios of the aperture widths of the bottom sides and the heights of the angle limiting filters 41, 42 are set in response to the transmission wavelength bands of the optical bandpass filters 61, 62 (e.g., BW1, BW2 to be described later with FIG. 10(B)). The aperture parts (hollow parts) of the angle limiting filters 41, 42 are formed using a material transparent with respect to the wavelengths detected by the photodiodes 31, 32, and formed (filled) by insulating layers of $SiO_2$ (silicon oxide films) or the like, for example.

The inclined structure 50 is formed on the angle limiting filters 41, 42, and has inclined surfaces at different inclination angles in response to the transmission wavelengths of the optical bandpass filters 61, 62. Specifically, a plurality of the inclined surfaces at the inclination angle $\theta1$ with respect to the surface of the semiconductor substrate 10 are formed on the photodiode 31, and a plurality of the inclined surfaces at the inclination angle $\theta2$ different from the inclination angle $\theta1$ are formed on the photodiode 32. As will be described later, the inclined structure 50 is formed by processing insulating films of $SiO_2$ or the like, for example, by etching or CMP, a gray-scale lithography technology, or the like.

The optical bandpass filters 61, 62 are formed by a multilayer thin film 70 stacked on the inclined structure 50. The transmission wavelength bands of the optical bandpass filters 61, 62 are determined by the inclination angles $\theta1, \theta2$ of the inclined structure 50 and the incident light limitation angles (aspect ratios) of the angle limiting filters 41, 42. The optical bandpass filters 61, 62 have configurations in which transmission wavelengths are varied in response to the inclination angles, and thus, not stacked at separate steps with respect to each transmission wavelength, but stacked at the same multilayer film forming step.

Note that the case where the optical sensor is the spectroscopic sensor has been explained as above, however, the embodiment is not limited to that. For example, the optical sensor of the embodiment may be applied to an illuminance sensor or an elevation sensor.

Here, the illuminance sensor is an optical sensor that measures illuminance (lux or lumen/square meter) of natural light and illumination light. In the embodiment, the incident angle is limited by the angle limiting filter and entrance of unwanted lights from other than the object to be measured may be limited. For example, application of the embodiment to a system that automatically lights a headlight of a bicycle in response to brightness in a traveling direction is considered. For example, when entering a tunnel, the system does not react with unwanted lights, and thereby, appropriate automatic lighting may be realized.

Further, the elevation sensor is an optical sensor that measures an elevation angle as an angle formed between a direction of the sun or an illumination light source and a reference surface. The reference surface is a horizontal surface, for example. In the embodiment, the incident angle is limited by the angle limiting filter, and thus, the elevation angle may be measured. For example, application of the embodiment to a solar power system is considered. In this case, the direction of the sun is measured with high accuracy and a solar panel is directed toward the direction, and thereby, high-efficiency power generation may be realized.

Now, in the optical sensor in related art, difficulty in downsizing is problematic. For example, in the spectroscopic sensor that acquires a continuous spectrum, it is necessary to provide a prism for generation of the continuous spectrum or the like and secure an optical path length, and the device becomes larger. Accordingly, it is difficult to provide many sensors and constantly provide sensors for an object to be inspected.

In this regard, according to the embodiment, photodiodes (light receiving elements) are formed by the impurity regions for photodiodes 31, 32 (impurity regions for light receiving elements) formed on the semiconductor substrate 10.

Further, in the embodiment, the angle limiting filters 41, 42 are formed using light blocking materials formed by the semiconductor process on the impurity regions for photodiodes 31, 32.

In this manner, the respective component elements of the optical sensor may be formed by the semiconductor process, and downsizing of the optical sensor or the like may be realized. That is, the photodiodes 31, 32 and the angle limiting filters 41, 42 are formed by the semiconductor process, and thereby, microfabrication may be easily performed and downsizing may be realized. Further, compared to the case where members are bonded, the transmission wavelength selectivity may be improved. Furthermore, compared to the case where optical fibers are used as the angle limiting filters, reduction of transmission light due to reduction of the limitation angle (numerical aperture) may be suppressed and the wavelength selectivity may be improved.

Here, the semiconductor process is a process in which transistors, resistor elements, capacitors, insulating layers, wiring layers, etc. are formed on a semiconductor substrate. For example, the semiconductor process is a process including an impurity introduction process, a thin-film formation process, a photolithography process, an etching process, a planarizing process, and a thermal treatment process.

Further, the light receiving regions of the photodiodes are regions on the impurity regions for photodiodes 31, 32 that incident lights that have passed through the angle limiting filters 41, 42 enter. For example, in FIG. 8, the regions correspond to the respective apertures of the lattice-shaped angle limiting filters 41, 42. Alternatively, in FIG. 9, the regions are regions (e.g., regions LRA) surrounded by the light blocking materials forming the angle limiting filters 41, 42.

Furthermore, the light blocking material is a light absorbing material or light reflection material. The light absorbing material is tungsten, for example, and the light reflection material is aluminum, for example.

Note that the angle limiting filters 41, 42 are not limited to the case where they are closed along the outer circumferences of the light receiving regions, but may have discontinuous parts along the outer circumferences or may be discontinuously provided along the outer circumferences.

Further, in the embodiment, the optical bandpass filters 61, 62 are formed by multilayer thin films inclined at the angles $\theta1, \theta2$ in response to the transmission wavelengths with respect to the semiconductor substrate 10. More specifically, the optical bandpass filters 61, 62 are formed by a plurality of sets of multilayer thin films having different transmission wavelengths. For example, as shown in FIG. 9, a plurality of multilayer thin films at the inclination angle θ1 are continuously arranged, and thereby, one set of multilayer thin films are formed. Alternatively, the multilayer thin films at the different inclination angles θ1, θ2 may be provided adjacent to each other, the multilayer thin films at the inclination angles θ1, θ2 may be repeatedly provided, and one set of multilayer thin films may be formed by the plurality of multilayer thin films at the same inclination angle (e.g., θ1).

In this manner, the optical bandpass filters 61, 62 may be formed by the multilayer thin films inclined at the angles θ1, θ2 in response to the transmission wavelengths. Thereby, it is not necessary to stack the multilayer thin films having film thicknesses in response to the transmission wavelengths at separate steps with respect to each transmission wavelength, and the forming step of the multilayer thin films may be simplified.

Further, the embodiment includes the inclined structure 50 provided on the angle limiting filters 41, 42. Furthermore, the inclined structure 50 has the inclined surfaces inclined at the angles θ1, θ2 in response to the transmission wavelengths of the optical bandpass filters 61, 62 with respect to the semiconductor substrate 10, and the multilayer thin films are formed on the inclined surfaces.

In this manner, the multilayer thin films are formed on the inclined surfaces of the inclined structure 50, and thereby, the multilayer thin films inclined at the angles θ1, θ2 in response to the transmission wavelengths of the optical bandpass filters 61, 62 may be formed.

5. Transmission Wavelength Bands of Optical Bandpass Filters

As described above, the transmission wavelength bands of the optical bandpass filters are set by the inclination angles of the multilayer thin films and the limitation angles of the angle limiting filters. In this regard, specific explanation will be made using FIGS. 10(A), 10(B). Note that, for simplicity of explanation, the case where the film thicknesses of the multilayer thin films of the optical bandpass filters 61, 62 are the same will be explained as an example as below, however, in the embodiment, the film thicknesses of the multilayer thin films of the optical bandpass filters 61, 62 may be different in response to the inclination angles θ1, θ2. For example, in the deposition of the thin films, when the thin films are grown in the direction perpendicular to the semiconductor substrate, the film thicknesses of the multilayer thin films of the optical bandpass filters 61, 62 may be proportional to cos θ1, cos θ2.

Figure 10A:
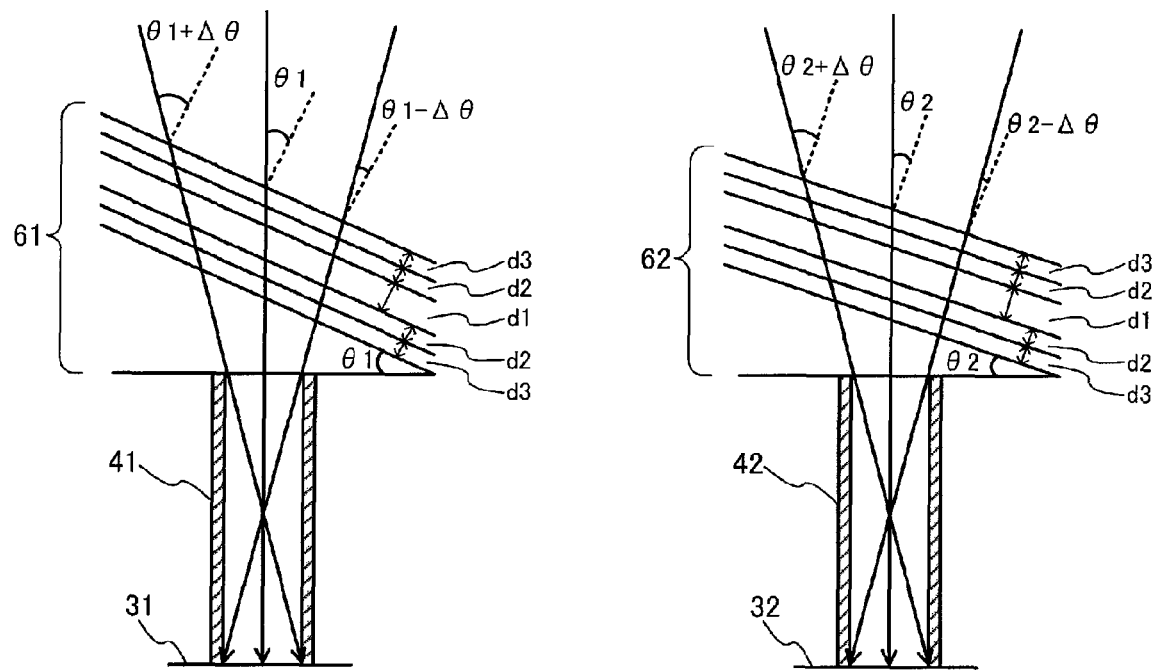
FIGS. 10(A) and 10(B) are explanatory diagrams of transmission wavelength bands of optical bandpass filters.

As shown in FIG. 10(A), the multilayer thin films of the optical bandpass filters 61, 62 are formed by thin films having thicknesses d1 to d3 (d2<d1, d3<d1). The thin films having the thicknesses d2, d3 are alternately stacked in pluralities of layers on and under the thin film having the thickness d1. The thin film having the thickness d2 is formed using a material having a different refractive index from those of the thin films having the thicknesses d1, d3. Note that, in FIG. 10(A), the numbers of layers of the thin films having the thicknesses d2, d3 are omitted for simplicity, however, actually, several tens to several hundreds of thin films are stacked on and under the thin film having the thickness d1. Further, in FIG. 10(A), one thin film having the thickness d1 is shown for simplicity, however, actually, a plurality of layers thereof are often formed.

The multilayer thin films of the optical bandpass filter 61 have the inclination angle θ1 with respect to the light receiving surface of the photodiode 31, and thereby, the light beams perpendicular to the light receiving surface enter at the angle of θ1 with respect to the multilayer thin films of the optical bandpass filter 61. Further, supposing that the limitation angle of the angle limiting filter 41 is Δθ, the light beams entering at θ1−Δθ to θ1+Δθ with respect to the multilayer thin films of the optical bandpass filter 61 reach the light receiving surface of the photodiode 31. Similarly, the light beams entering at θ2−Δθ to θ2+Δθ with respect to the multilayer thin films of the optical bandpass filter 62 reach the light receiving surface of the photodiode 32.

Figure 10B:
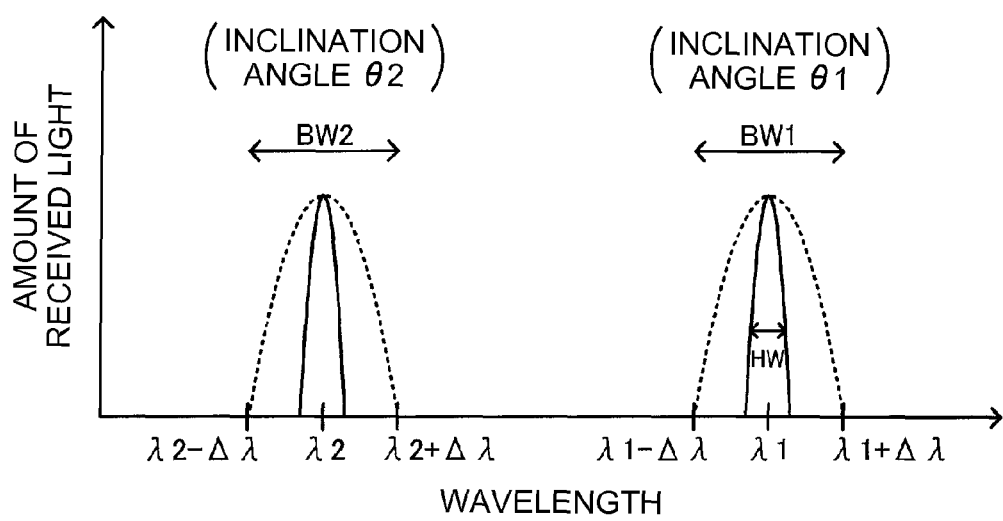

As shown in FIG. 10(B), the transmission wavelength band BW1 of the optical bandpass filter 61 is λ1−Δλ to λ1+Δλ. In this regard, the transmission wavelength with respect to the light beam at the incident angle θ1 is λ1=2×n×d1×cos θ1. Here, n is the refractive index of the thin film having the thickness d1. Further, λ1−Δλ=2×n×d1×cos(θ1+Δθ), λ1+Δλ=2×n×d1×cos(θ1−Δθ). The half width HW of the transmission wavelength with respect to the light beam at the incident angle θ1 (e.g., HW<BW1) is determined by the number of stacked layers of the multilayer films. The amount of received light of the photodiode 31 is the maximum at the incident angle θ1 perpendicular to the light receiving surface and zero at the limitation angle, and thereby, the amount of received light in the incident lights as a whole is shown by the curve of a dotted line. Similarly, the transmission wavelength band BW2 of the optical bandpass filter 62 is λ2−Δλ to λ2+Δλ. For example, in the case of θ2>θ1, λ2=2×n×d1×cos θ2<λ1=2×n×d1×cos θ1.

Note that the limitation angles of the angle limiting filters 41, 42 are set to Δθ≤30°. Desirably, the limitation angles of the angle limiting filters 41, 42 are set to Δθ≤20°.

6. Manufacturing Method

An example of a method of manufacturing the spectroscopic sensor of the embodiment when the inclined structure is formed by the semiconductor process will be explained using FIG. 11. Note that the more detailed manufacturing method is disclosed in JP-A-2011-203247, for example.

Figure 11:
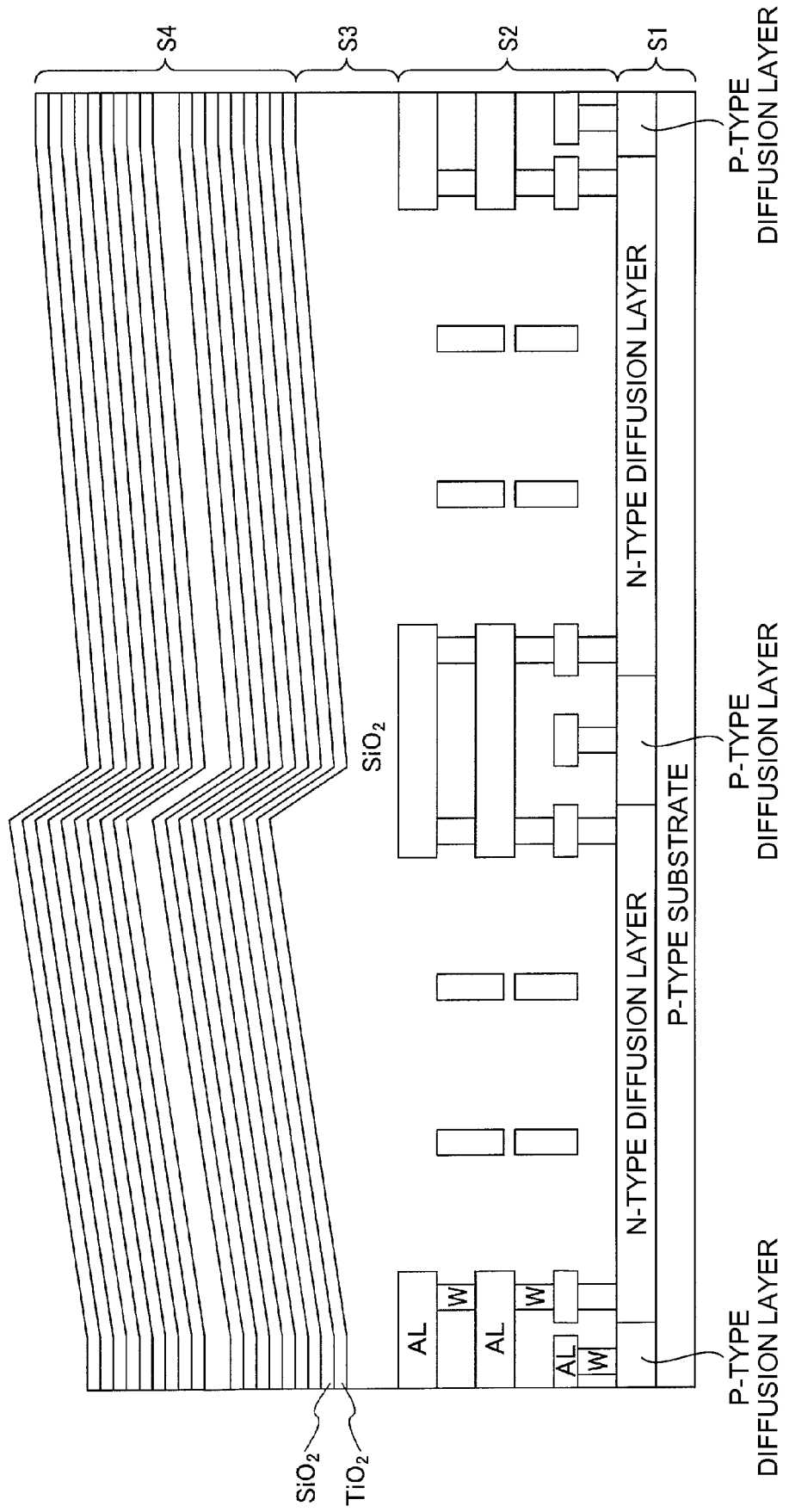
FIG. 11 shows a manufacturing method example of the optical sensor.

First, as shown by S1 in FIG. 11, N-type diffusion layers (impurity regions of photodiodes) are formed on a P-type substrate, and P-type diffusion layers are formed on the P-type substrate. The N-type diffusion layers serve as cathodes of the photodiodes and the P-type diffusion layers (P-type substrate) serve as anodes.

Then, as shown by S2, insulating films are formed, contact holes are formed in the insulating film, the contact holes are embedded, and thereby, first AL wires are formed. Then, at the same step as above, via contacts and second AL wires are formed, and the step is repeated at the necessary number of times. FIG. 11 shows the example in which the third AL wires have been formed. Then, insulating films are formed and the planarizing step of the insulating films by CMP is performed. Through the above described wiring forming steps, the AL wires and tungsten plugs forming the angle limiting filters are stacked.

Then, as shown by S3, insulating films having level differences or density patterns are formed by anisotropic dry etching of deposited SiO$_2$, a polishing step by CMP is performed on the insulating films, and thereby, the inclined surfaces of the inclined structure are formed.

Then, as shown by S4, sputtering of TiO₂ (titanium oxide film) and sputtering of SiO₂ are alternately performed, and thereby, multilayer thin films are formed on the inclined surfaces. The TiO₂ film is a thin film having a higher refractive index and the SiO₂ film is a thin film having a lower refractive index.

In the above description, the case where the angle limiting filters are formed by the wiring process has been explained as an example, however, the embodiment is not limited to that, but the angle limiting filters may be formed by drilling the semiconductor substrate from the rear surface, for example (e.g., JP-A-2011-205088). Further, in the above description, the case where the inclined structure is formed integrally with the angle limiting filters by the semiconductor process has been explained as an example, however, the embodiment is not limited to that, but the inclined structure may be separately formed using a die or the like, for example, and the inclined structure may be bonded onto the angle limiting filters (e.g., JP-A-2011-203247).

7. Electronic Apparatus

Figure 12:
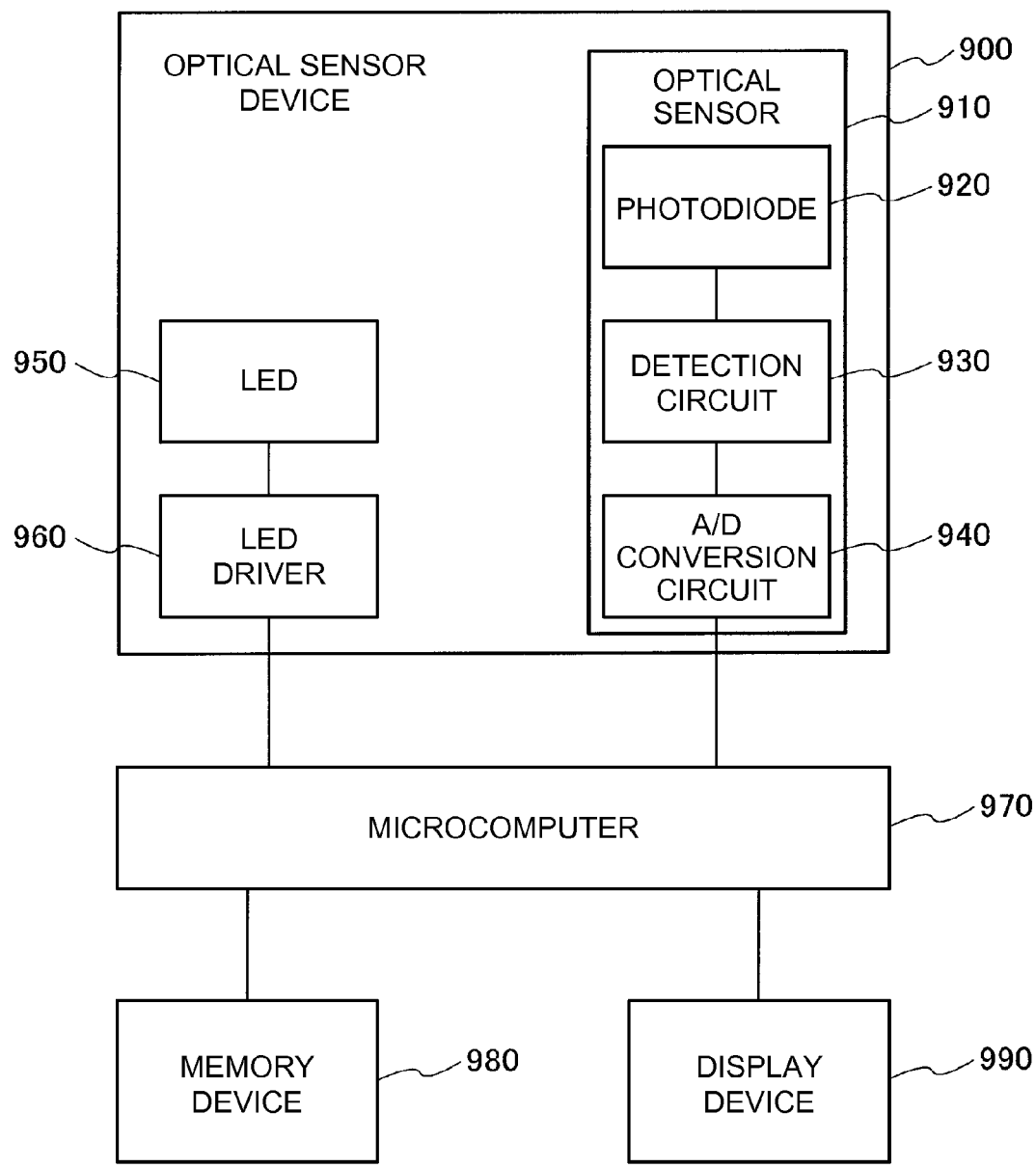
FIG. 12 shows a configuration example of an electronic apparatus.

FIG. 12 shows a configuration example of an electronic apparatus of the optical sensor of the embodiment. For example, as the electronic apparatus, a pulsimeter, a pulse oximeter, a blood glucose level measuring instrument, a fruit saccharimeter, or the like is assumed. Note that the embodiment is not limited to the configuration in FIG. 12, but, for example, an LED 950 may be omitted and used for an elevation angle measuring instrument, an illuminometer, or the like.

The electronic apparatus shown in FIG. 12 includes an optical sensor device 900, a microcomputer 970 (CPU), a memory device 980, and a display device 990. The optical sensor device 900 includes the LED 950 (light source), an LED driver 960, and an optical sensor 910. The optical sensor 910 is integrated in a one-chip IC, for example, and includes a photodiode 920, a detection circuit 930, and an A/D conversion circuit 940.

The LED 950 irradiates an object to be observed with white light, for example. The optical sensor device 900 spectroscopically separates reflection lights and transmission lights from the object to be observed, and acquires signals having respective wavelengths. The microcomputer 970 controls the LED driver 960 and acquires signals from the optical sensor 910. The microcomputer 970 displays display based on the acquired signals on the display device 990 (e.g., a liquid crystal display device) and stores data based on the acquired signals in the memory device 980 (e.g., a memory, a magnetic disc).

Note that the embodiment has been explained in detail as described above, however, a person who skilled in the art could readily understand that many modifications may be made without substantially departing from the new matter and effects of the invention. Therefore, the modified examples may fall within the scope of the invention. For example, in the specification or drawings, the terms described with the broader or synonymous different terms at least once may be replaced by the different terms in any part of the specification or drawings. Further, the configurations and operations of the optical sensor, the electronic apparatus, etc. are not limited to those explained in the embodiment, but various modifications may be made.

The invention claimed is:

1. An optical sensor comprising:
   a light receiving element;
   an optical filter that transmits a light having a specific wavelength of incident lights with respect to a light receiving region of the light receiving element; and
   an angle limiting filter that limits an incident angle of the incident lights transmitted through the optical filter, wherein the angle limiting filter comprises a plurality of light block material columns that extend through an entire thickness of the angle limiting filter,
   wherein, a limitation angle of the angle limiting filter is θA, a height from an upper surface of the angle limiting filter to an upper surface of the optical filter is RTP, and a distance from an end of the optical filter to an end of an aperture of an outermost light blocking material column of the plurality of light blocking material columns of the angle limiting filter in a plan view with respect to the upper surface of the angle limiting filter is an overlap distance OV, and wherein the angle limiting filter is configured to satisfy $\tan^{-1}(OV/RTP) > \theta A$ so that light passing through a side wall surface of the optical filter, between the upper surface of the optical filter and a lower surface of the optical filter, does not enter the light receiving element.

2. The optical sensor according to claim 1, wherein a width of the aperture of the angle limiting filter is d and a height of the angle limiting filter is RA, the limitation angle is $\theta A = \tan^{-1}(d/RA)$.

3. The optical sensor according to claim 1, further comprising:
   a protective film disposed between the angle limiting filter and the optical filter,
   wherein,
   a height of the protective film is RP and a height of the optical filter is RT, the height from the upper surface of the angle limiting filter to the upper surface of the optical filter is RTP=RP+RT.

4. The optical sensor according to claim 1, wherein a wavelength of the incident light is λ, the height of the angle limiting filter is RA, and the width of the aperture of the angle limiting filter is d, $d^2/(\lambda \times RA) \geq 2$ is satisfied.

5. The optical sensor according to claim 2, wherein the limitation angle satisfies $\theta A = \tan^{-1}(d/RA) < 60°$.

6. The optical sensor according to claim 1, wherein the optical sensor is a spectroscopic sensor for spectroscopically separating the incident light.

7. The optical sensor according to claim 1, wherein the optical sensor is an illuminance sensor for measuring illuminance of the incident light.

8. The optical sensor according to claim 1, wherein the optical sensor is an elevation sensor for measuring an elevation angle of a light source.

9. An electronic apparatus comprising the optical sensor according to claim 1.

10. The optical sensor of claim 1, wherein the optical filter comprises a short-pass filter (SPF).

11. The optical sensor of claim 1, wherein the optical filter comprises a long-pass filter (LPF).

12. The optical sensor of claim 1, wherein the optical filter comprises a short-pass filter and a long-pass filter.

* * * * *